(12) United States Patent
Panin et al.

(10) Patent No.: US 7,856,129 B2
(45) Date of Patent: Dec. 21, 2010

(54) ACCELERATION OF JOSEPH'S METHOD FOR FULL 3D RECONSTRUCTION OF NUCLEAR MEDICAL IMAGES FROM PROJECTION DATA

(75) Inventors: Vladimir Panin, Knoxville, TN (US); Frank Kehren, Knoxville, TN (US); Christian J. Michel, Lenior City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 956 days.

(21) Appl. No.: 11/716,359

(22) Filed: Mar. 9, 2007

(65) Prior Publication Data

US 2008/0219525 A1 Sep. 11, 2008

(51) Int. Cl.
 *G06K 9/00* (2006.01)
(52) U.S. Cl. ...................................... 382/128; 382/131
(58) Field of Classification Search ................. 382/128, 382/131
 See application file for complete search history.

(56) References Cited

U.S. PATENT DOCUMENTS

2008/0180580 A1 * 7/2008 Kadrmas .................... 348/744

* cited by examiner

*Primary Examiner*—John B Strege
(74) *Attorney, Agent, or Firm*—Peter L. Kendall (57) ABSTRACT

A method for interpolating at least one oblique line of response ray representing nuclear image projection data through a rectangular volume and a system for using the method. The method consists of steps of interpolating all the direct rays in a rectangular volume, making a projected ray by projecting the oblique ray onto a surface of the rectangular volume, matching the projected ray to a coinciding interpolated direct ray, shearing the rectangular volume to match the projected ray, and interpolating the oblique ray in the sheared volume.

21 Claims, 6 Drawing Sheets

ACCELERATION OF JOSEPH'S METHOD FOR FULL 3D RECONSTRUCTION OF NUCLEAR MEDICAL IMAGES FROM PROJECTION DATA

TECHNICAL FIELD

The current invention is in the field of medical imaging, and in particular pertains to reconstruction of tomographic images from acquired projection data obtained by an imaging apparatus.

BACKGROUND OF THE INVENTION

Medical imaging is one of the most useful diagnostic tools available in modern medicine. Medical imaging allows medical personnel to non-intrusively look into a living body in order to detect and assess many types of injuries, diseases, conditions, etc. Medical imaging allows doctors and technicians to more easily and correctly make a diagnosis, decide on a treatment, prescribe medication, perform surgery or other treatments, etc.

There are medical imaging processes of many types and for many different purposes, situations, or uses. They commonly share the ability to create an image of a bodily region of a patient, and can do so non-invasively. Examples of some common medical imaging types are nuclear medical (NM) imaging such as positron emission tomography (PET) and single photon emission computed tomography (SPECT). Using these or other imaging types and associated apparatus, an image or series of images may be captured. Other devices may then be used to process the image in some fashion. Finally, a doctor or technician may read the image in order to provide a diagnosis.

A PET camera works by detecting pairs of gamma ray photons in time coincidence. The two photons arise from the annihilation of a positron and electron in the patient's body. The positrons are emitted from a radioactive isotope that has been used to label a biologically important molecule (a radiopharmaceutical). Hundreds of millions such decays occur per second in a typical clinical scan. Because the two photons arising from each annihilation travel in opposite directions, the rate of detection of such coincident pairs is proportional to the amount of emission activity, and hence the molecule, along the line connecting the two detectors at the respective points of gamma ray interaction. In a PET camera the detectors are typically arranged in rings around the patient. By considering coincidences between all appropriate pairs of these detectors, a set of projection views can be formed, each element of which represents a line integral, or sum, of the emission activity in the patient's body along a well defined path. These projections are typically organized into a data structure called a sinogram, which contains a set of plane parallel projections at uniform angular intervals around the patient. A three dimensional image of the radiopharmaceutical's distribution in the body then can be reconstructed from these data.

A SPECT camera functions similarly to a PET camera, but detects only single photons rather than coincident pairs. For this reason, a SPECT camera must use a lead collimator with holes, placed in front of its detector panel, to pre-define the lines of response in its projection views. One or more such detector panel/collimator combinations rotates around a patient, creating a series of planar projections each element of which represents a sum of the emission activity, and hence biological tracer, along the line of response defined by the collimation. As with PET, these data can be organized into sinograms and reconstructed to form an image of the radiopharmaceutical tracer distribution in the body.

The purpose of the reconstruction process is to retrieve the spatial distribution of the radiopharmaceutical from the projection data. A conventional reconstruction step involves a process known as back-projection. In simple back-projection, an individual data sample is back-projected by setting all the image pixels along the line of response pointing to the sample to the same value. In less technical terms, a back-projection is formed by smearing each view back through the image in the direction it was originally acquired. The back-projected image is then taken as the sum of all the back-projected views. Regions where back-projection lines from different angles intersect represent areas which contain a higher concentration of radiopharmaceutical.

While back-projection is conceptually simple, it does not by itself correctly solve the reconstruction problem. A simple back-projected image is very blurry; a single point in the true image is reconstructed as a circular region that decreases in intensity away from the center. In more formal terms, the point spread function (PSF) of back-projection is circularly symmetric, and decreases as the reciprocal of its radius.

Filtered back-projection (FBP) is a technique to correct the blurring encountered in simple back-projection. Each projection view is filtered before the back-projection step to counteract the blurring point spread function. That is, each of the one-dimensional views is convolved with a one-dimensional filter kernel (e.g. a "ramp" filter) to create a set of filtered views. These filtered views are then back-projected to provide the reconstructed image, a close approximation to the "correct" image.

The inherent randomness of radioactive decay and other processes involved in generating nuclear medical image data results in unavoidable statistical fluctuations (noise) in PET or SPECT data. This is a fundamental problem in clinical imaging that is dealt with through some form of smoothing of the data. In FBP this is usually accomplished by modifying the filter kernel used in the filtering step by applying a low-pass windowing function to it. This results in a spatially uniform, shift-invariant smoothing of the image that reduces noise, but may also degrade the spatial resolution of the image. A disadvantage of this approach is that the amount of smoothing is the same everywhere in the image although the noise is not. Certain regions, e.g. where activity and detected counts are higher, may have relatively less noise and thus require less smoothing than others. Standard windowed FBP cannot adapt to this aspect of the data.

There are several alternatives to FBP for reconstructing nuclear medical data. In fact, most clinical reconstruction of PET images is now based on some variant of regularized maximum likelihood (RML) estimation because of the remarkable effectiveness of such algorithms in reducing image noise compared to FBP. In a sense, RML's effectiveness stems from its ability to produce a statistically weighted localized smoothing of an image. These algorithms have some drawbacks however: they are relatively expensive because they must be computed iteratively; they generally result in poorly characterized, noise dependent, image bias, particularly when regularized by premature stopping (unconverged); and the statistical properties of their image noise are difficult to determine.

In a class of algorithms for calculating projections known as the Square Pixel Method, the basic assumption is that the object considered truly consists of an array of N×N square pixels, with the image function $f(x, y)$ assumed to be constant over the domain of each pixel. The method proceeds by evaluating the length of intersection of each ray with each pixel, and multiplying the value of the pixel (S).

The major problem of this method is the unrealistic discontinuity of the model. This is especially apparent for rays whose direction is exactly horizontal or vertical, so that relatively large jumps occur in S values as the rays cross pixel boundaries.

A second class of algorithms for calculating projections is the forward projection method. This method is literally the adjoint of the process of "back projection" of the FBP reconstruction algorithm. The major criticism of this algorithm is that the spatial resolution of the reprojection is lessened by the finite spacing between rays. Furthermore, increasing the number of pixels does not contribute to a reduction in this spacing, but does greatly increase processing time.

A third algorithm for calculating projections based on line-integral approximation, developed by Peter M. Joseph and described in the paper entitled *An Improved Algorithm for Reprojecting Rays Through Pixel Images*, IEEE Transactions on Medical Imaging, Vol. MI-1, No. 3, pp. 192-196, November 1982 (hereinafter, "Joseph's Method"), incorporated by reference herein in its entirety, is similar to the structure of the square pixel method. Each given ray K is specified exactly as a straight line. The basic assumption is that the image is a smooth function of x and y sampled on the grid of positions. The line integral desired is related to an integral over either x or y depending on whether the ray's direction lies closer to the x or y axis. While this algorithm produces a much clearer image than the other two methods, it is slower than either method, especially when interpolating oblique segments. When interpolating oblique segments, an interpolation is required in both the transaxial and axial directions for each ray, further slowing the process.

Therefore, there exists a need in the art to have a method for calculating projections that has the clarity of Joseph's Method yet takes less processing time.

SUMMARY OF THE INVENTION

Provided is a method for reconstructing a tomographic image from projection data by interpolating an oblique ray or line of response (LOR) through a rectangular volume having the steps of: interpolating all the direct rays in a rectangular volume, creating a projected ray by projecting the oblique ray onto a surface of the rectangular volume, matching the projected ray to a coinciding interpolated direct ray, shearing the rectangular volume to match the projected ray, and interpolating the oblique ray in the sheared volume.

Further provided is a method for interpolating a number of oblique rays through a rectangular volume having the steps of: interpolating all the direct rays in a rectangular volume, creating a plurality of projected rays for each oblique ray by projecting the oblique rays onto a surface of the rectangular volume, matching each projected ray to a coinciding interpolated direct ray, creating a plurality of sheared volumes by shearing the rectangular volume to match the projected rays, and interpolating each oblique ray in each sheared volume.

Further provided is a method for interpolating at least two oblique rays of opposite polar angle through a rectangular volume having the steps of: interpolating all the direct rays in a rectangular volume, projecting the of oblique rays of opposite polar angle onto a surface of the rectangular volume, matching the projected rays to a coinciding interpolated direct ray, creating sheared volumes for each projected ray by shearing the rectangular volume to match the projected rays, interpolating one oblique ray of opposite polar angle in its corresponding sheared volume, and applying the interpolated value to the rest of the oblique rays of opposite polar angle.

Further provided is a system for reconstructing tomographic images from projection data by interpolating oblique rays or LORs. The system includes a medical imaging device, a processor, and software running on the processor that executes the methods of the present invention.

BRIEF DESCRIPTION OF THE DRAWINGS

The invention will now be described in greater detail in the following by way of example only and with reference to the attached drawings, in which.

DETAILED DESCRIPTION OF THE INVENTION

As required, disclosures herein provide detailed embodiments of the present invention; however, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

Figure 1:
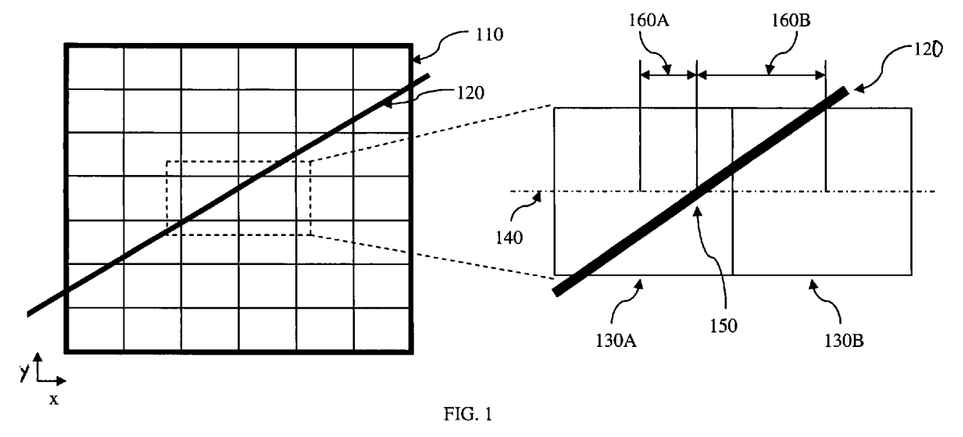
FIG. 1 is a representation of Joseph's Method for two dimensional interpolation.

Joseph's Method is a method for reprojecting rays through pixel images using line integrals. The basic assumption is that the image is a smooth function of x and y sampled on a grid of points in (x,y) space. FIG. 1 is a representation of Joseph's Method in two dimensional space 110. Each ray 120 passing through space 110, is specified as a straight line, using either:

$$y(x) = -\cot(\theta)x + y_0$$

or $$x(y) = -y\tan(\theta) + x_0.$$

The line integral desired is related to an integral over either x or y depending on whether ray 120's direction lies closer to the x or y axis, that is $$S(K) = \int_{L_k} ds f(x, y)$$

or $$= \frac{1}{|\sin(\theta)|} \int f(x, y(x)) dx \text{ for } |\sin(\theta)| \geq \frac{1}{\sqrt{2}}$$

$$= \frac{1}{|\cos(\theta)|} \int f(x(y), y) dy \text{ for } |\cos(\theta)| \geq \frac{1}{\sqrt{2}}.$$

The above two equations are related in the interchange of x and y as independent and dependent variables.

In each case, the one dimensional integral is approximated by a simple sum, such as a Riemann sum; for example, the x-direction integral becomes $$S = \frac{1}{|\sin\theta|} \left[ \sum_{n=2}^{N-1} P_{n,n'} + \lambda_n (P_{n,n'+1} - P_{n,n'}) + T_1 + T_N \right]$$

where the terms $T_1$ and $T_N$ represents the first and last pixel on the line and are treated separately, and $\lambda_n$ is the fractional number defined by $n'$=integer part of $y(x_n)$ $\lambda_n = y(x_n) - n'$.

Interpolation enters in two senses: 1) explicitly, in the use of fraction $\lambda_n$ to estimate the value of $f(x_n, y(x_n)) \approx (1-\lambda_n) P_{n,n'} + \lambda_n P_{n,n'+1}$ and 2) implicitly in the sense that the summation above is the application of the trapezoidal rule to numerically estimate the one dimensional (x) integral.

The treatment of the endpoints $T_1$ and $T_N$ depend on the application. In some situations, they may be taken to be zero if outside the object images. For applications to heart-isolating algorithms, it is necessary to make them proportional to the length of intersection of the ray with the first and last pixels.

Looking at FIG. 1, in two dimensions, Joseph's Method can be summarized as follows: For a given line or row y in two-dimensional space 110, each ray 120 receives information from the two nearest pixels 130A and 130B. The distances 160A and 160B between the centers of pixels 130A and 130B and the point 150 where ray 120 intersects the horizontal line 140 passing through the center of pixels 130A and 130B define the interpolation coefficients.

Figure 11A:
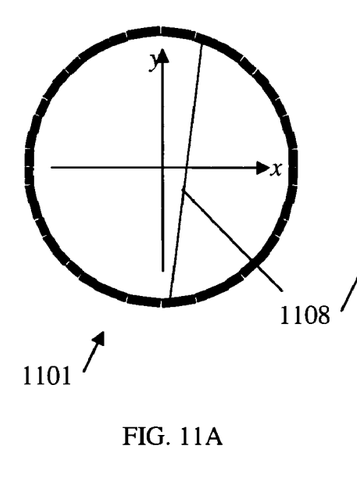
FIGS. 11A and 11B are top and cross-sectional views, respectively, of a cylindrical PET scanner with multiple detector rings, which is applicable to the present invention.
Figure 11B:
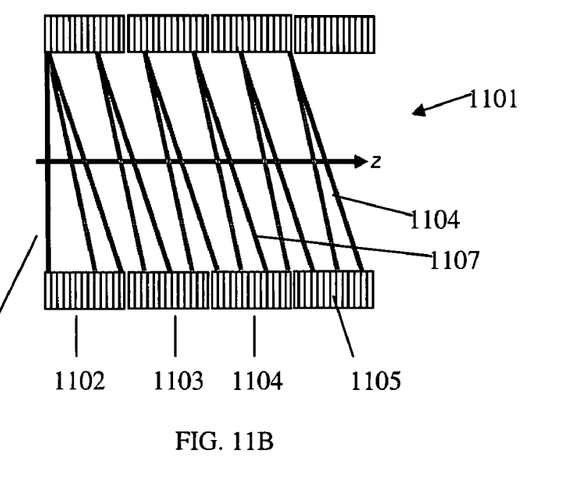

When there is translational symmetry in the axial (z) direction, the interpolation coefficients are the same for all the rays which differ only by their axial coordinate. This is shown in FIGS. 11A-11B, which is a schematic representation of a cylindrical PET scanner 1101, and its cross-section, respectively. The PET scanner 1101 includes multiple detector rings, such as rings 1102-1105. Oblique rays 1106 and 1107 correspond to various non-zero ring difference. For example, ray 1106 extends between rings 1104 and 1105, while ray 1107 extends between rings 1103 and 1104. Rays 1106 and 1107 have the same transaxial coordinates (in the x-y plane) as direct rays 1108, which extends within the same detector ring 1102. There is also an axial translation symmetry for all rays with the same ring difference.

Figure 2A:
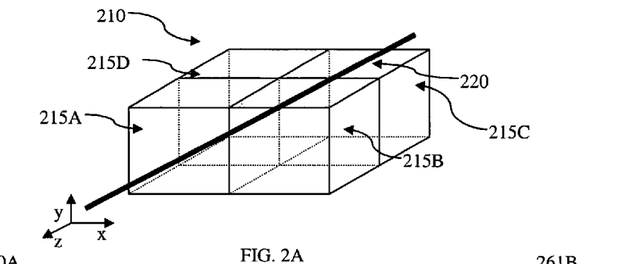
FIGS. 2A-C are three dimensional, front, and side views, respectively, of a oblique ray in a rectangular volume.
Figure 2B:
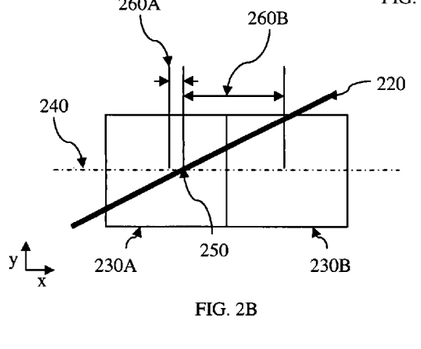
Figure 2C:
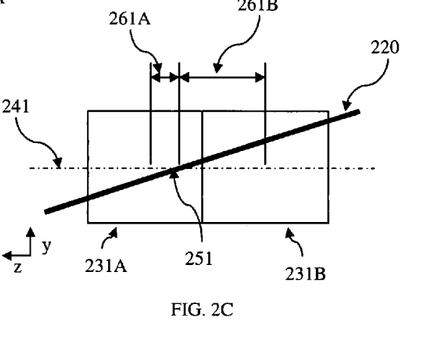

FIG. 2A is an example of an oblique segment ray 220 in three dimensional space 210. Oblique segment ray 220 receives information from the four nearest voxels (i.e., volume elements or three dimensional pixels) 215A, 215B, 215C and 215D in an (x,y,z) image volume: the four voxels can be broken down into four pixels, two pixels 230A and 230B in the x direction (FIG. 2B), and two pixels 231A and 231B in the axial or z direction (FIG. 2C).

In order to interpolate oblique ray 220, interpolations over both the x direction and the z direction must be made. As in the two dimensional case, the distances 260A and 260B between the centers of pixels 230A and 230B and the point 250 where the ray 220 intersects the horizontal line 240 passing through the center of pixels 230A and 230B define the interpolation coefficients in the x direction. Likewise, the distances 261A and 261B between the centers of pixels 231A and 231B and the point 251 where the ray 220 intersects the horizontal line 241 passing through the center of pixels 231A and 231B, define the interpolation coefficients in the axial direction.

Figure 3:
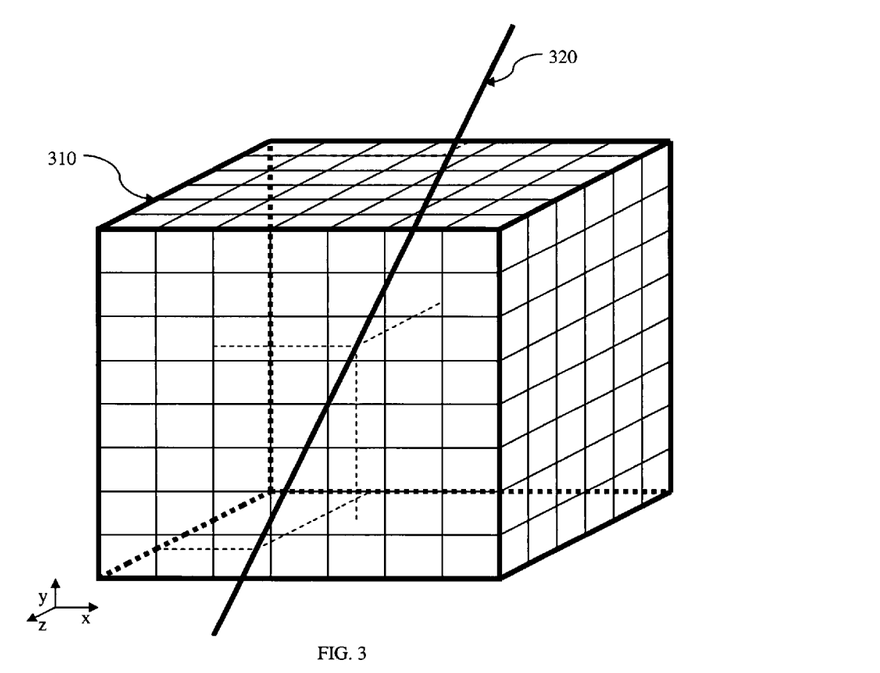
FIG. 3 is a representation of Joseph's Method for three dimensional interpolation.

FIG. 3 shows an example of an oblique ray 320 in a rectangular image volume 310 for a full three-dimensional reconstruction. If one were to interpolate based on Joseph's Method as described above, both front (i.e. xy) surface 410A and side (i.e. yz) surface 410B projections of the oblique ray 320 (see FIGS. 4A and 4B) would be necessary for each such oblique ray 320, thus creating a front ray projection 420A and a side ray projection 420B.

Figure 4A:
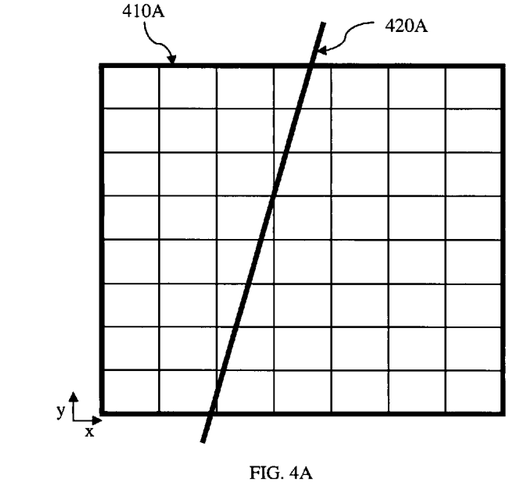
FIG. 4A-B are front and side views, respectively, of the three dimensional interpolation of FIG. 3.
Figure 4B:
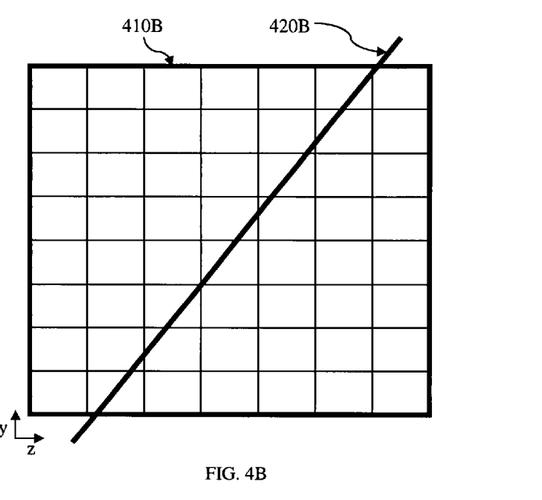

However, front ray projection 420A of oblique ray 320 on front surface 410A may coincide with the projection of a direct (i.e. two dimensional) ray on the same plane. Therefore, the interpolation coefficients in the x direction may be the same for front ray projection 420A of oblique ray 320 and the direct two-dimensional ray. The pixel interpolation values for the direct rays thus could be reused on front ray projection 420A.

Figure 5:
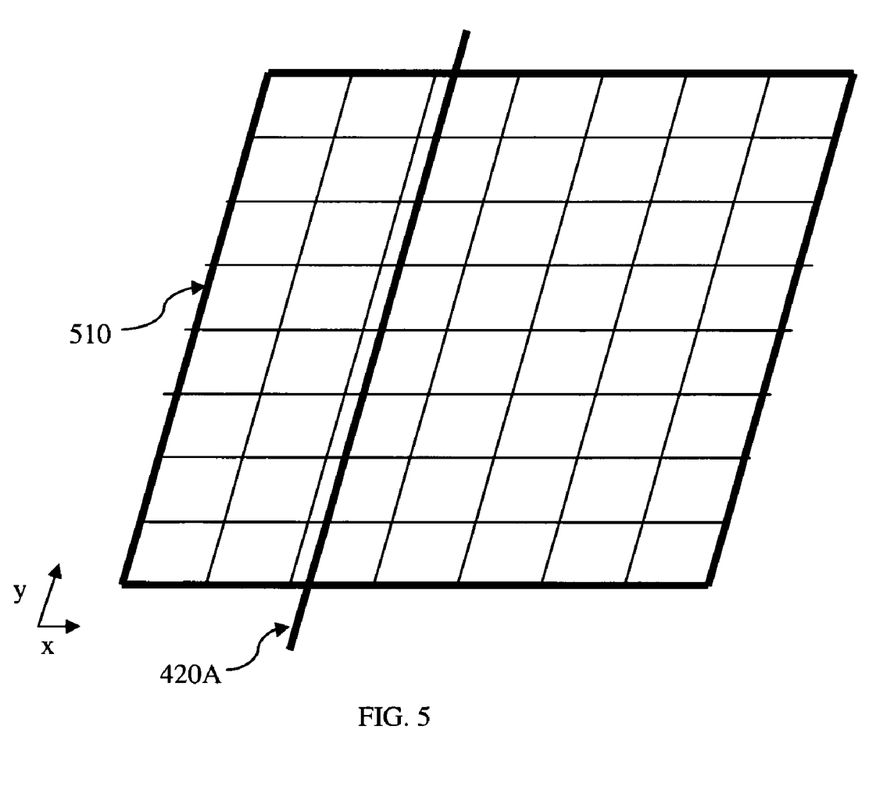
FIG. 5 is a front view of a sheared space for the three dimensional interpolation of FIG. 3 in accordance with the present invention.

An efficient way to use such interpolated pixel values over the whole image volume would be to compute a sheared volume 510 (see FIG. 5). In sheared volume 510, in each row from volume 310 of FIG. 3, the vertical edges of the voxels may be skewed so that they are aligned with front ray projection 420A on the xy surface.

By so shearing the volume space to create sheared volume 510 to match the direction of ray projection 420A, the two interpolations otherwise needed for oblique ray 320 may be reduced to a single interpolation of oblique ray 320 in sheared volume 510. When there is translational symmetry in the z direction as shown in FIG. 11, the interpolation coefficients may be the same for all the rays which differ only by their x coordinate. Therefore, only one interpolation coefficient can be used for all voxels of one axial row in the sheared volume. This coefficient may be different for each plane.

Figure 6:
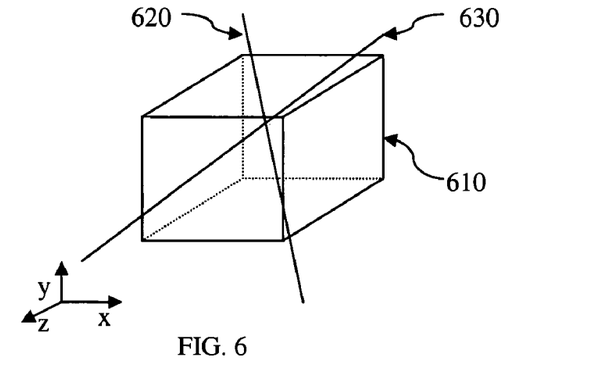
FIG. 6 is a three dimensional space with two opposite polar angle rays passing through it.
Figure 7A:
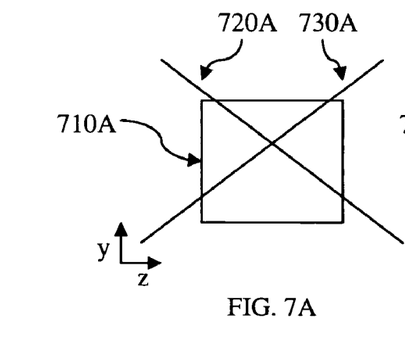
FIGS. 7A and 7B are front and side views, respectively, of the three dimensional space of FIG. 6.
Figure 7B:
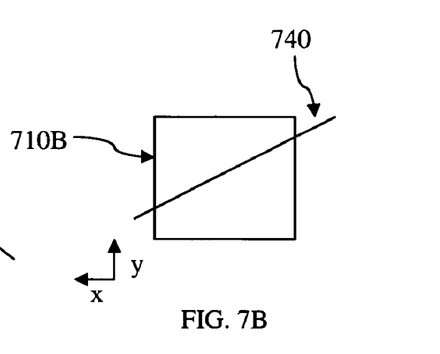

FIG. 6 shows a three dimensional space 610 through which model ray 620 and model ray 630 pass. Model rays 620 and 630 have opposite polar angles (i.e. opposite angles in the y-z plane). When rays 620 and 630 are projected onto the xy side surface 710B (see FIG. 7B), it can be seen that they both have the identical xy side surface projection 740. Yet, when model rays 620 and 630 are projected onto the yz front surface 710A (see FIG. 7A), it can be seen that they have opposite or mirrored yz front surface projections 720A and 730A.

Figure 8A:
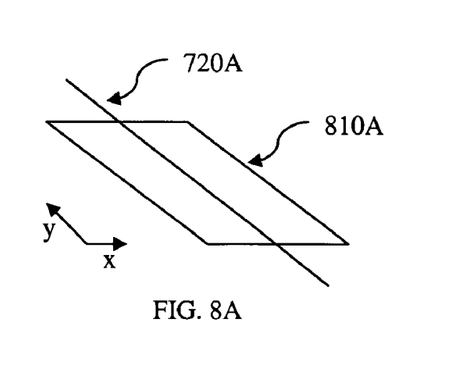
FIGS. 8A and 8B are the front views of the sheared space for the two rays in FIG. 6.
Figure 8B:
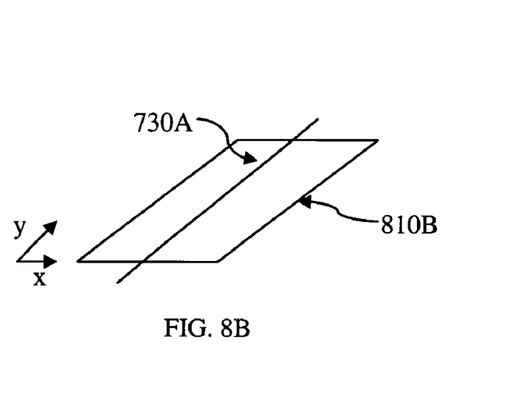

FIGS. 8A and 8B show front views of sheared volumes 810A and 810B for front projections 720A and 730A in accordance with the present invention. While sheared volumes 810A and 810B are different, each front projection 720A and 730A may coincide with a projection of a direct ray on the same plane. In practice, the same sheared volume may be used for both positive and negative polar angles, such that only one of the volumes 810A and 810B is actually necessary.

Once the sheared volumes 810A or 810B are matched to the direct rays, the interpolation may reduce to a single interpolation of oblique model rays 620 and 630 in the sheared volume 810A or 810B, respectively. Since both model rays 620 and 630 have the same side projection 740, both rays can be interpolated in the same single interpolation.

For example, an oblique ray in a positive segment uses the following one dimensional axial interpolation:

$$P_{positive\ segment} = value = w_z * shearedvoxel(\rho,y,z) + (1-w_z) * shearedvoxel(\rho,y,z+1)$$

While the same ray in the negative segment reuses the coefficients as:

$$P_{negative\ segment} = (1-w_z) * shearedvoxel(\rho,y,z) + w_z * shearedvoxel(\rho,y,z+1) = shearedvoxel(\rho,y,z) + shearedvoxel(\rho,y,z+1) - value$$

This excludes multiplication when calculating rays for one of the segments for the voxels in the sheared volume belonging to the intersection of the two segments. The algorithm may be thus summarized as follows.

The equations for Joseph's method can be rewritten for the 3D case as:

$$y(x) = -\cot(\theta)x + y_0$$

$$z(x) = d(x)\tan\phi + z_0 = \left(-x\frac{1}{\sin\theta} + d_0\right)\tan\phi + z_0, \quad |\sin\theta| \geq \frac{1}{\sqrt{2}}$$

or $$x(y) = -y\tan(\theta) + x_0$$

$$z(y) = d(y)\tan\phi + z_0 = \left(y\frac{1}{\cos\theta} + d_0\right)\tan\phi + z_0, \quad |\cos\theta| \geq \frac{1}{\sqrt{2}}$$

and thus $$S(K) = \frac{1}{|\sin\theta\cos\varphi|}\int f(x, y(x), z(x))dx, \quad |\sin\theta| \geq \frac{1}{\sqrt{2}}$$

$$= \frac{1}{|\cos\theta\cos\varphi|}\int f(x(y), y, z(x))dx, \quad |\cos\theta| \geq \frac{1}{\sqrt{2}}$$

Where $\theta$ is the azimuthal and $\phi$ is the polar angle. For the case where $$|\sin\theta| \geq \frac{1}{\sqrt{2}}$$

$$S = \frac{1}{|\sin\theta\cos\phi|}\left[\sum_{n=2}^{N-1} \mu_n(P_{n,n',n''} + \lambda_n(P_{n,n'+1,n''} - P_{n,n',n''})) + (1-\mu_n)(P_{n,n',n''+1} + \lambda_n(P_{n,n'+1,n''+1} - P_{n,n',n''+1}))\right]$$

where
n'=integer part of $y(x_n)$
$\lambda_n = y(x_n) - n'$.
n''=integer part of $z(x_n)$
$\mu_n = z(x_n) - n''$
where $P_{n,n',n''} = f(n,n',n'')$.

For each azimuthal angle, a sheared volume is calculated using a 1D transaxial interpolation in the original volume. Because of the transaxial symmetry, the original and sheared volumes are stored with axial index first. An array of depth coordinates d is also computed, as such coordinates are used when computing interpolation factors for oblique segments. Projection rays are also stored with axial index first. The storage of the axial index as the first index is very important from a hardware point of view, as all operations are applied in axial direction first. Thus, having the axial index as the first index facilitates an efficient use of the memory cache and enables use of hardware parallelization. This results in fast computing. The projections for 2D segments are calculated at the same time as the sheared volumes. The projections for all oblique segments are then obtained by a 1D axial interpolation in the sheared volume.

Figure 9:
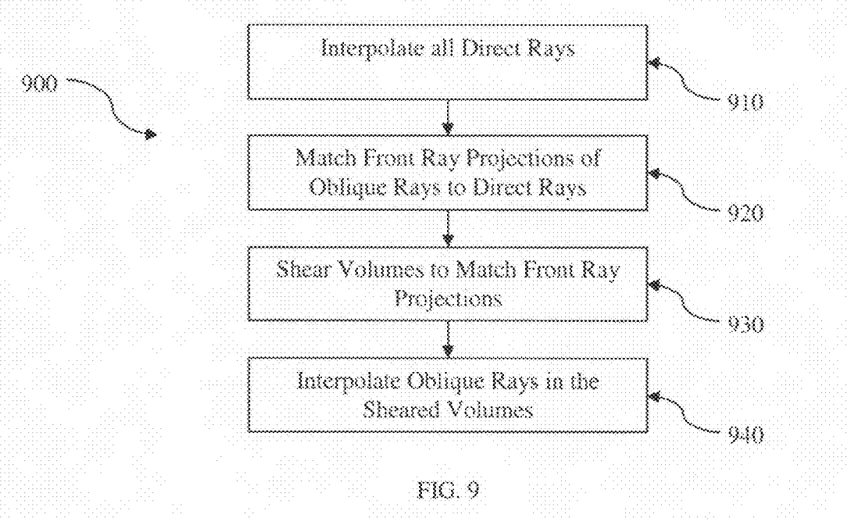
FIG. 9 is a flow chart of a method according to the present invention.

FIG. 9 shows an embodiment of a method 900 in accordance with the present invention. The first step 910 is to interpolate all the direct (i.e. planar) rays in the image volume. Once there are a number of direct rays, in step 920 the front surface ray projections of the oblique rays may be matched to the direct rays. The voxel space may then be sheared at step 930 to align with the matched front ray projections. Finally, the oblique rays may be interpolated at step 940 in the sheared volumes.

Figure 10:
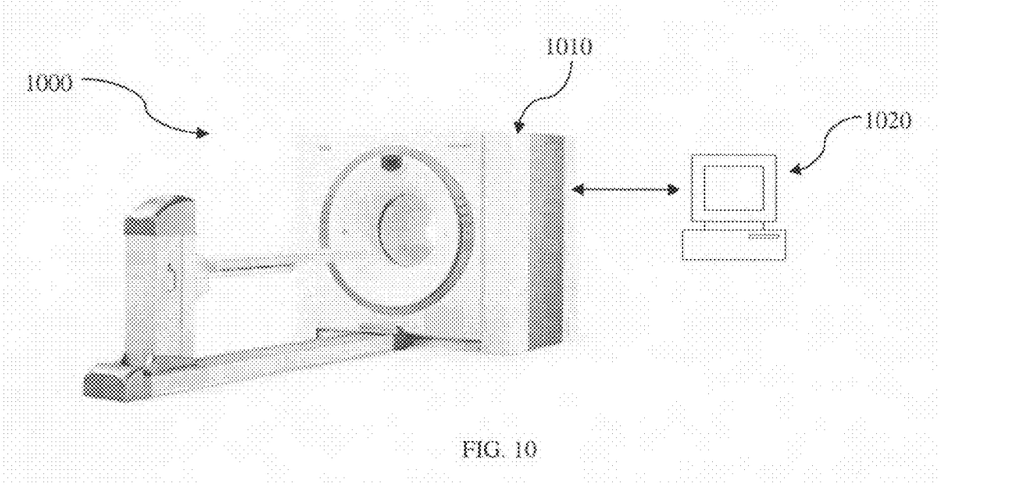
FIG. 10 is a system using the methods of the present invention.

FIG. 10 is a system 1000 for using method 900. System 1000 may be comprised of a medical imaging device 1010, i.e. a PET scanner, a SPECT scanner or similar device capable of acquiring a medical image. Medical imaging device 1010 may be attached to a processor 1020 for receiving the data. Processor 1020 may have software running on it that executes a method of the present invention and outputs a fully three dimensional reconstruction of the object scanned.

The invention having been thus described, it will be apparent to those skilled in the art that the same may be varied in many ways without departing from the spirit of the invention. Any and all such variations are intended to be covered within the scope of the following claims. For example, the method can be extended to a so-called LOR projection geometry when the transverse distance between rays is not a constant, as in a ring scanner. In such case, the method requires only a scanner with axial translation symmetry. The method also can be extended in the case of an unmatched back-projector. In such case, a different shear procedure would be used where each voxel receives contributions from two nearest projection rays in the transverse direction. This is important when the transverse voxel size is significantly smaller than the transverse projection size.

What is claimed is:

1. A method performed by a processor for reconstructing a nuclear medical image in three-dimensional image space by interpolating contributions of oblique line-of-response projection rays through a rectangular volume to voxels of said volume, comprising the steps of:
    (a) interpolating contributions of all direct rays through said rectangular volume;
    (b) creating surface projected rays by projecting said oblique line-of-response rays onto a surface of the rectangular volume;
    (c) matching the projected rays to coinciding interpolated direct rays;
    (d) shearing the rectangular volume to align with matched projected rays; and
    (e) interpolating matched projected rays in corresponding sheared volumes.

2. The method of claim 1, wherein step (a) is accomplished by Joseph's Method.

3. The method of claim 2, wherein Joseph's Method consists of the steps of:
(i) measuring the distances between the centers of the two pixels nearest the ray and the point where the ray intersects the line passing through the center of the pixels, and
(ii) using the measured distances as the coefficients for interpolation.

4. The method of claim 1, wherein step (e) is accomplished using Joseph's Method.

5. The method of claim 4, wherein Joseph's Method consists of the steps of:
(i) measuring the distances between the centers of the two pixels nearest the ray and the point where the ray intersects the line passing through the center of the pixels, and
(ii) using the measured distances as the coefficients for interpolation.

6. The method of claim 1, further comprising the step of using the interpolation from a first oblique ray for additional oblique rays that have translational symmetry with the first oblique ray along one axis of the rectangular volume.

7. The method of claim 1, wherein step (d) is accomplished by skewing rows of voxels in the rectangular volume so that the voxels' vertical edges are substantially parallel to the projected ray.

8. A method for interpolating contributions of at least two oblique line of response rays representing nuclear medical image projection data of opposite polar angles through a rectangular image volume to voxels of said volume, comprising the steps of:
(a) interpolating all direct line of response rays in said rectangular volume;
(b) projecting said oblique rays of opposite polar angles onto a surface of the rectangular volume;
(c) matching the projected rays to coinciding interpolated direct rays;
(d) creating sheared volumes for each projected ray by shearing the rectangular volume to align with the angle of the matched projected rays;
(e) interpolating one oblique ray of opposite polar angle in its corresponding sheared volume; and
(f) applying the interpolated value to the rest of the oblique rays of opposite polar angle.

9. The method of claim 8, wherein step (a) is accomplished using Joseph's Method.

10. The method of claim 9, wherein Joseph's Method consists of the steps of:
(i) measuring the distances between the centers of the two pixels nearest the ray and the point where the ray intersects the line passing through the center of the pixels, and
(ii) using the measured distances as the coefficients for interpolation.

11. The method of claim 8, wherein step (e) is accomplished using Joseph's Method.

12. The method of claim 11, wherein Joseph's Method consists of the steps of:
(i) measuring the distances between the centers of the two pixels nearest the ray and the point where the ray intersects the line passing through the center of the pixels, and
(ii) using the measured distances as the coefficients for interpolation.

13. The method of claim 8, wherein step (d) is accomplished by skewing the rows of voxels in the rectangular volume so that the voxels' vertical edges are substantially parallel to the projected rays.

14. A system for reconstructing nuclear medical images by interpolation of oblique line of response ray contributions to voxels in an image volume, comprising:
a medical imaging device;
a processor for receiving data from the medical imaging device; and
software executing on the processor, wherein the software interpolates all direct rays in said image volume, creates a plurality of projected rays for each oblique ray by projecting the oblique line of response rays onto a surface of the image volume, matches each projected ray to a coinciding interpolated direct ray, creates a plurality of sheared volumes by shearing the image volume to align with matched projected rays, and interpolates each oblique line of response ray in each sheared volume.

15. The system of claim 14, wherein the software interpolates using Joseph's Method.

16. The system of claim 15, wherein the software executes Joseph's Method by measuring the distances between the centers of the two pixels nearest the ray and the point where the ray intersects the line passing through the center of the pixels, and using the measured distances as the coefficients for interpolation.

17. The system of claim 14, wherein the medical imaging device is a PET scanner.

18. The system of claim 14, wherein the medical imaging device is a SPECT scanner.

19. The system of claim 14, wherein the software outputs a full three dimensional image reconstruction.

20. The system of claim 19, said three dimensional reconstruction is displayed on a graphical interface.

21. The system of claim 19, wherein said full three dimensional reconstruction is outputted as a data set.

* * * * *